(12) United States Patent
Uehara et al.

(10) Patent No.: US 6,885,726 B2
(45) Date of Patent: Apr. 26, 2005

(54) FLUORESCENT X-RAY ANALYSIS APPARATUS

(75) Inventors: Yasushi Uehara, Tokyo (JP); Teruo Shibano, Tokyo (JP)

(73) Assignee: Mitsubishi Denki Kabushiki Kaisha, Tokyo (JP)

( * ) Notice: Subject to any disclaimer, the term of this patent is extended or adjusted under 35 U.S.C. 154(b) by 16 days.

(21) Appl. No.: 10/419,964

(22) Filed: Apr. 22, 2003

(65) Prior Publication Data

US 2004/0109534 A1 Jun. 10, 2004

(30) Foreign Application Priority Data

Dec. 5, 2002 (JP) ........................................ 2002-353663

(51) Int. Cl.⁷ .......................................... G01N 23/223
(52) U.S. Cl. ............................. 378/44; 378/45; 378/84; 378/145
(58) Field of Search ............................. 378/44, 45, 46, 378/47, 48, 49, 50, 53, 54, 82, 83, 85, 145

(56) References Cited

U.S. PATENT DOCUMENTS

| | | | | |
|---|---|---|---|---|
| 6,023,496 A | * | 2/2000 | Kuwabara | .................... 378/45 |
| 6,226,347 B1 | * | 5/2001 | Golenhofen | ................. 378/45 |
| 6,442,236 B1 | | 8/2002 | Utaka | .......................... 378/84 |

FOREIGN PATENT DOCUMENTS

| | | |
|---|---|---|
| JP | 11-052096 | 2/1999 |
| JP | 2001-133421 | 5/2001 |

\* cited by examiner

Primary Examiner—Edward J. Glick
Assistant Examiner—Courtney Thomas
(74) Attorney, Agent, or Firm—Leydig, Voit & Mayer, Ltd.

(57) ABSTRACT

A fluorescent X-ray analysis apparatus includes: an X-ray generation source for radiating a beam of primary X-rays; spectroscopic elements circularly arranged so that their inner surfaces describe a circle centered on an optical axis of the beam of primary X-rays for monochromatizing the beam of primary X-rays and condensing the beam on a surface of an irradiation object; a spectroscopic element position adjuster for adjusting the positions of the spectroscopic elements; secondary X-rays detector for detecting secondary X-rays radiated from the surface of the irradiation object irradiated with the monochromatized beam of primary X-rays; a secondary X-ray detector position adjuster adjusting the position of the secondary X-ray detector; an irradiation object surface position detector detecting the position of the surface of the irradiation object; and a controller adjusting the positions of the spectroscopic elements through the spectroscopic element position adjuster to condense the monochromatized beam of primary X-rays on the surface of the irradiation object, on the basis of the position of the surface of the irradiation object detected by the irradiation object surface position detector.

8 Claims, 4 Drawing Sheets

FLUORESCENT X-RAY ANALYSIS APPARATUS

BACKGROUND OF THE INVENTION

1. Field of the Invention

This invention relates to a fluorescent X-ray analysis apparatus, and particularly to a fluorescent X-ray analysis apparatus for monitoring the concentration of an element in a liquid, and the composition or thickness of a thin film during a manufacturing process.

2. Description of the Related Art

A fluorescent X-ray analysis apparatus is used for measuring the composition of various materials and the thickness of a film during an electronic device manufacturing process or the like. An ordinary fluorescent X-ray analysis apparatus has an analysis chamber, which increases the scale of the apparatus, and conventionally the apparatus is only used in sampling inspection for evaluation of the samples. Recently, however, in order to improve the yield and quality of products in manufacture of semiconductors, it has become increasingly necessary to analyze the composition of various materials and the thickness of a film during a manufacturing process, and an analysis apparatus capable of in-line monitoring of the composition and the film thickness has been required.

Recently, while portable fluorescent X-ray analysis apparatuses are developed and commercially available, the focal position of an irradiation X-ray is fixed to one point (surface of an apparatus). (See Japanese Laid-Open Patent Publication 2001-133421, pages 3–4, FIG. 1 and FIG. 2)

During an actual manufacturing process, it is almost impossible to install an irradiation object constantly at a predetermined position and the surface height of the irradiation object often changes. Therefore, if the focal position of an irradiation X-ray is fixed on the surface of the fluorescent X-ray analysis apparatus, a moving means for moving the entire fluorescent X-ray analysis apparatus is necessary. However, the conventional portable fluorescent X-ray analysis apparatus is adapted for simplified analysis and has no such moving means. It has no detecting means for detecting the changing surface position of the irradiation object, either. Moreover, the conventional portable fluorescent X-ray analysis apparatus basically requires that a sample has a smooth surface, and miniaturization of the apparatus limits the quantity of X-ray irradiation. Therefore, a detector for a secondary X-ray must be arranged very closely to the irradiation object, and even when a moving means is provided, the apparatus cannot be applied to in-line monitoring.

SUMMARY OF THE INVENTION

A fluorescent X-ray analysis apparatus according to this invention enables change of the focal position of an irradiation X-ray (primary X-ray) in accordance with a change of the surface position of an irradiation object in order to monitor the concentration of a metal element in various liquids, the composition of a thin film, the thickness of the film or the like in an in-line process. This secures stable irradiation intensity (intensity per unit area) of the primary X-ray on the surface of the irradiation object and also secures stable intensity of a secondary X-ray that is necessary for in-line process monitoring of the composition of the surface of the irradiation object, the thickness of the film or the like.

Since the fluorescent X-ray analysis apparatus according to this invention includes: an X-ray generation source for radiating a primary X-ray; plural spectroscopic elements circularly arranged so that their inner surfaces constitute a circle centering on an optical axis of the primary X-ray and adapted for monochromatizing and condensing the primary X-ray on a surface of an irradiation object; a spectroscopic element position adjusting means for adjusting the positions of the plural spectroscopic elements; a secondary X-ray detector for detecting a secondary X-ray radiated from the surface of the irradiation object upon irradiation with the monochromatized primary X-ray; a secondary X-ray detector position adjusting means for adjusting the position of the secondary X-ray detector; an irradiation object surface position detecting means for detecting the position of the surface of the irradiation object; and a control means for adjusting the positions of the plural spectroscopic elements by the spectroscopic element position adjusting means so as to condense the monochromatized primary X-ray on the surface of the irradiation object, on the basis of information of the position of the surface of the irradiation object detected by the irradiation object surface position detecting means, the primary X-ray having necessary intensity for analysis can be accurately irradiated onto the surface position of the irradiation object even when the surface position of the irradiation object changes. Thus, a fluorescent X-ray analysis apparatus that enables monitoring an element of various liquids with changing surface positions, composition of a thin film, the thickness of the film and the like in an in-line process is realized.

DESCRIPTION OF THE PREFERRED EMBODIMENTS

Embodiment 1

Figure 1:
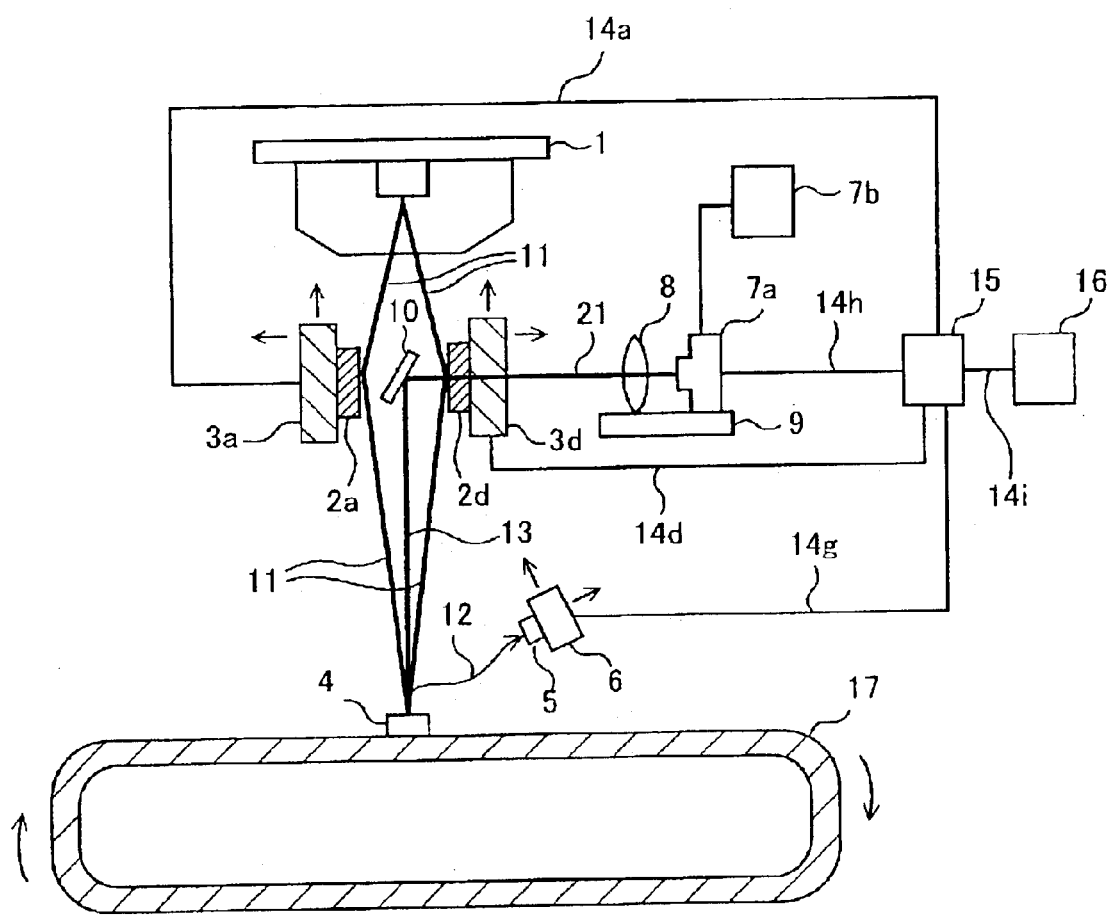
FIG. 1 is an explanatory view showing a cross-sectional structure of a fluorescent X-ray analysis apparatus according to this invention.
Figure 2:
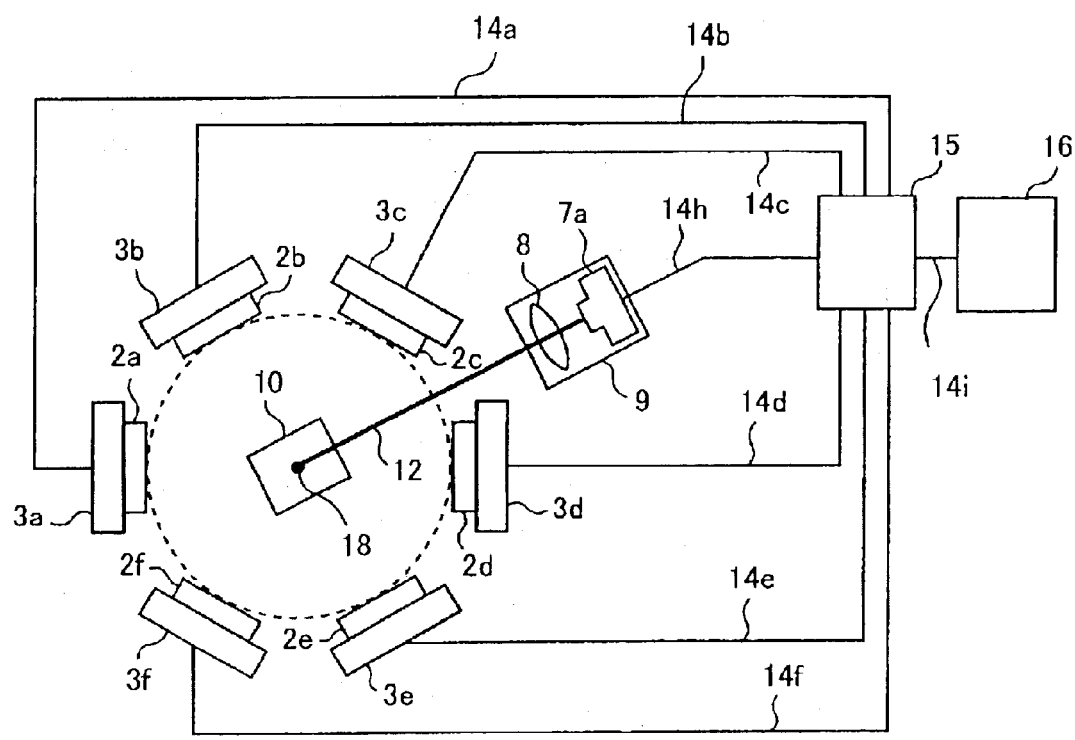
FIG. 2 is an explanatory view showing a top structure of the fluorescent X-ray analysis apparatus according to this invention.

FIG. 1 is an explanatory view showing a cross-sectional structure of a fluorescent X-ray analysis apparatus according to this invention. FIG. 2 is an explanatory view showing a structure of the fluorescent X-ray analysis apparatus of FIG. 1 as viewed from its top. The operation of the apparatus will now be described with reference to the drawings.

A primary X-ray 11 radiated from an X-ray tube (X-ray generation source) 1 is spectrally divided by spectroscopic elements 2a to 2f and the primary X-ray 11 is monochromatized. (In FIG. 1, only 2a and 2b are shown.) Monochromatization of the primary X-ray 11 is for the purpose of improving the analytic sensitivity of the fluorescent X-ray analysis apparatus. Specifically, the primary X-ray 11 radiated from the X-ray tube 1 usually has a certain width of wavelengths. However, if the primary X-ray 11 has a width of wavelengths, it becomes a noise source in generation and detection of a secondary X-ray, which will be described later, and the analytic sensitivity is lowered. Therefore, it is desired that the primary X-ray 11 irradiated on the surface of a sample (irradiation object) 4 to generate the secondary X-ray is monochromatized (to a single wavelength), if possible.

The monochromatization of the primary X-ray 11 by the spectroscopic elements 2a to 2f is based on the following principle. That is, on the assumption that the spacing of lattice planes of crystal of the spectroscopic elements is represented by d, the angle of incidence of the primary X-ray is represented by θ, the reflection order is represented by n and the wavelength of the primary X-ray is represented by λ, when these satisfy the relation of the Bragg's formula expressed by the following equation (1), the primary X-ray is reflected. On the other hand, a primary X-ray that does not satisfy this relation is not reflected. As a result, only the primary X-ray with a specified wavelength (λ) incident at a specified angle (θ) is reflected and monochromatized.

$$2d \cdot \sin \theta = n \cdot \lambda \tag{1}$$

The monochromatized primary X-ray 11 is irradiated on the surface of the sample 4. As shown in FIG. 2, the spectroscopic elements 2a to 2f have their inner surfaces arranged at circumferential positions (indicated by a dotted line in FIG. 2) of a circle centering on an optical axis 18 (central axis of the primary X-ray 11 radiated at a predetermined angle of radiation) of the primary X-ray 11 so that the monochromatized primary X-ray 11 forms a focal point (which means condensation of the X-ray) on the surface of the sample 4.

The reason why the spectroscopic elements are arranged so that the monochromatized primary x-ray 11 forms a focal point on the surface of the sample 4 is that the quantity of a secondary X-ray radiated from the surface of the sample 4 is proportional to the irradiation intensity per unit area of the primary X-ray 11 on the surface of the sample 4. When the primary X-ray 11 is reflected by the spectroscopic elements 2a to 2f in accordance with equation (1) and irradiated on the surface of the sample 4, if the primary X-ray 11 is irradiated on different positions on the surface of the sample 4, the irradiation intensity per unit area of the primary X-ray 11 on the surface of the sample 4 is not improved. However, as the spectroscopic elements 2a to. 2f are arranged on circumferential positions of a circle centering on an optical axis 18 (central axis of the primary X-ray radiated at a predetermined angle of radiation) of the primary X-ray 11 the primary X-ray 11 reflected by the spectroscopic elements 2a to 2f is condensed at one point on the surface of the sample 4 (center of optical axis of the primary X-ray 11 on the surface of the sample 4), and the irradiation intensity per unit area of the primary X-ray 11 on the surface of the sample 4 is improved. Therefore, the quantity of the secondary X-ray radiated from the surface of the sample 4 increases and the analytic accuracy is improved accordingly. As the spectroscopic elements, LiF or super-lattice crystal can be used as in the conventional apparatus.

In the case the spectroscopic elements 2a to 2f are flat, in theory, only one point of each of the spectroscopic elements 2a to 2f satisfies the relation of equation (1) and therefore the direction of each spectroscopic elements is not particularly important. However, in consideration of easiness of design and adjustment, the spectroscopic elements are usually arranged in parallel to the above-described center of optical axis of the primary X-ray.

When the monochromatized primary X-ray 11 is irradiated on the surface of the sample 4, a secondary X-ray 12 corresponding to an element constituting the surface of the sample 4 is radiated from the surface of the sample 4. The secondary X-ray 12 radiated from the surface of the sample 4 is detected by a secondary X-ray detector 5. This secondary X-ray 12 includes X-rays of various wavelengths. The analysis of wavelength components or energy components allows the surface composition of the sample 4 to be found. In this invention, a silicon drift-type semiconductor detector, which is an energy dispersive detector, is used for the secondary X-ray detector 5, as in the conventional portable fluorescent X-ray analysis apparatus.

The energy dispersive detector analyzes an energy component of the secondary X-ray and transforms the analyzed energy component to a wavelength component on the basis of the following equation (2).

$$E = h/\lambda \tag{2}$$

In this equation, E represents the energy of the X-ray, h represents a Planck constant, and represents the wavelength of the X-ray. In this invention, the energy dispersive detector is used for the secondary X-ray detector for the following reason. That is, generally, the energy dispersive detector has lower sensitivity than a wavelength dispersive detector for analyzing a wavelength component, but the energy dispersive detector has a simple structure and does not require a large space, thus reducing the size of the apparatus. Moreover, unlike the wavelength dispersive detector, the energy dispersive detector need not analyze the component of the secondary X-ray while changing the inclination of the spectroscopic elements. Therefore, the energy dispersive detector is advantageous in that it enables fast detection, and it is suitable for in-line process monitoring. Furthermore, unlike the conventional Si (Li) detector, the silicon drift-type semiconductor detector need not be cooled by using liquid nitrogen. It is an essential constituent element for eliminating a vacuum chamber in fluorescent X-ray analysis.

The silicon drift-type semiconductor detector is described in detail in "Nuclear Instruments & Methods in Physics Research A, 377 (1996)."

Meanwhile, in the case of a conventional stationary fluorescent X-ray analysis apparatus, since the surface of the sample 4 is usually fixed at a predetermined position, the X-ray tube 1 and the spectroscopic elements 2a to 2f need not particularly adjust the position corresponding to individual samples. However, in the case of in-line monitoring, the sample 4 is put on a feed mechanism such as a belt 17 shown in FIG. 1 and a height adjustment mechanism is not provided in most cases. When the height of the sample 4 changes because of a change in thickness of the sample 4 itself, a change in height of the belt 17 or the like, this change directly leads to a change of analysis position.

In the case the fluorescent X-ray analysis apparatus is used for in-line monitoring, the purpose is often simplified monitoring of sample components or the like and position control with high accuracy as in the conventional stationary fluorescent X-ray analysis apparatus is not necessary. Usually, the surface of the sample 4 must be placed within a range of height of approximately ±0.5 mm from the focal position of the primary X-ray. Therefore, when the height of the sample changes by ±0.5 mm or more because of difference in height of the sample itself and difference in height of the feed mechanism, the positions (height) of the X-ray tube 1 and the spectroscopic elements 2a to 2f must be adjusted.

This adjustment of the height of the sample surface is carried out so that the above-described relation of equation (1) holds between the surface of the sample 4, the X-ray tube 1 and the spectroscopic elements 2a to 2f. Adjustment methods for this are roughly classified into the case of adjusting the positions of both the X-ray tube 1 and the spectroscopic elements 2a to 2f so as to fix the angle of incidence of the primary X-ray on the spectroscopic elements 2a to 2f, and the case of fixing the X-ray tube 1 and adjusting only the positions of the spectroscopic elements 2a to 2f on the assumption of a change in angle of incidence of the primary X-ray on the spectroscopic elements 2a to 2f.

In this invention, the X-ray tube 1 is fixed as shown in FIGS. 1 and 2 with respect to the sample 4 with a changing surface position, and moving mechanisms capable of moving in triaxial directions, for example, moving devices (spectroscopic element position adjusting means) 3a to 3f constituted as triaxial movement stages are provided on the spectroscopic elements 2a to 2f, respectively, thus maintaining the above-described relation of equation (1). The moving devices 3a to 3f are connected with a controller 15 by connection lines 14a to 14f. Also an irradiation object surface position detecting unit including a camera part 7a made up of a light source, a CCD camera and a detector, and a monitor part 7b, is connected with the controller 15. Data of the surface position of the sample 4 measured by the detector of the camera part 7a is sent to the controller 15 via a connection line 14h. The camera part 7a has a light source, not shown. This light source emits light 21 for sample monitoring and this light 21 is preset to be condensed on the surface of the sample 4 by a lens 8 and a reflection mirror 10. An image of the surface state of the sample 4 is picked up by the CCD camera of the camera part 7a and projected on the monitor part 7b. In the state where the relation between the X-ray tube 1 and the spectroscopic elements 2a to 2f is adjusted so that the surface position of the sample 4 satisfies the above-described equation (1), the position of the lens 8 is adjusted and the positions of the camera part 7a and the surface of the sample 4 are adjusted in advance.

Since the arrangement is adjusted in this manner, a change of the surface position of the sample 4 can be found by monitoring the image of the sample surface on the monitor 7b. An operator operates a control terminal 16 to move a stage 9 while watching the monitor 7b, then adjusts the positions of the camera part 7a and the lens 8 to find their positions that produce a clear image of the sample surface, calculates the quantity of change of the position of the sample 4 from its initial position, and sends the measured value to the controller 15. The controller 15 sends the calculated data to the moving devices 3a to 3f and adjusts the positions of the spectroscopic elements 2a to 2f so that the relation of equation (1) holds between the X-ray tube 1 and the sample 4. Since measuring objects in in-line monitoring are various materials such as liquids and thin films, when monitoring a sample with a changing surface position, the operator often carries out manual operations. However, if when the sample 4 has a flat surface, it is possible to binarize the contrast of the image at the end parts of the sample and automatically detect the surface position of the sample 4, using a so-called knife-edge method.

When the surface position or the angle of the sample 4 changes, the radiation position or the direction of radiation of the secondary X-ray 12 radiated from the surface of the sample 4 changes and therefore the position of the secondary X-ray detector 5 needs to be adjusted. Therefore, in the fluorescent X-ray analysis apparatus according to this invention, a stage (secondary X-ray detector position adjusting means) 6 for position adjustment is provided in the secondary X-ray detector 5, thus setting a position in accordance with the change of the surface position of the sample 4 on the basis of an instruction from a control means made up of the controller 15 and the control terminal 16 and carrying out position adjustment in consideration of the change in surface angle near this set position. Specifically, while the stage 6 is moved in X- and Y-directions, which are orthogonal to each other, within a predetermined range (for example, an area of ±5 cm), the secondary X-ray detector 5 is set at a position where the quantity of detection of the secondary X-ray 12 reaches the maximum. In this case, the stage 6 need not be a triaxial stage as long as it can be moved in the X- and Y-directions.

While a silicon drift-type semiconductor detector is used for the secondary X-ray detector 5 in the above-described embodiment, plural PIN semiconductor detectors may be used for the secondary X-ray detector 5. Since PIN semiconductor detectors need not be cooled, unlike a silicon drift-type semiconductor detector, and have various sizes and shapes, the degree of freedom in arrangement of the detectors increases. However, PIN semiconductor detectors have no energy resolution. Therefore, a certain measure needs to be taken to perform spectrally divide the X-ray energy using PIN semiconductor detectors. For this reason, a metal foil is arranged to cover detection windows in at least one part of the plural detectors, thus detecting a fluorescent X-ray via the metal foil. For example, when an element to be detected is copper (Cu), if a cobalt (Co) foil with a thickness of 15 $\mu$m is arranged, the foil absorbs approximately 90% of a fluorescent X-ray of Cu. Therefore, the intensity of the fluorescent X-ray of Cu can be estimated from the difference between detected value of the X-ray and a detector having no foil installed therein. When the concentration of n or more types of elements needs to be measured, it is possible to estimate the intensity of a fluorescent X-ray of each element by arranging (n+1) or more detectors and an appropriate metal foil.

Moreover, by installing the above-described fluorescent X-ray analysis apparatus, for example, at a position where a plating solution of a plating film forming apparatus can be observed such as a plating forming tank or a plating solution flow path, it is possible to automatically monitor the concentration of a metal element in the plating solution without carrying out a work such as extraction of the plating, solution. The liquid level of the solution used in the plating apparatus usually changes because of ripples and swelling due to circulation and because of natural evaporation. However, the above-described fluorescent X-ray analysis apparatus allows, the focal point of the primary X-ray to be constantly matched the liquid level and the concentration to be monitored with high accuracy. When the monitored value is lowered to value less than a predetermined one, by adding a device for automatically supplementing a predetermined ingredient, it becomes possible to perform plating under constant conditions and to stabilize and improve the quality of the plating film.

Furthermore, when the above-described fluorescent X-ray analysis apparatus is installed at a position where the surface of a sample can be observed in a thin film forming chamber of a thin film forming device such as an evaporation device or a sputtering device, or in a sample carrier system, it is possible to monitor the thickness of a thin film formed in the device by monitoring the intensity of a fluorescent X-ray of a thin film formed on the surface of the sample. In such a manufacturing device, the position where a sample is installed is usually decided and therefore an operation to constantly change the focal position of the primary X-ray is not necessary. However, by using the fluorescent X-ray analysis apparatus according to this invention, it is possible to decide the focal position in accordance with the existing thin film forming device and therefore to improve the degree of freedom in installation.

As described above, with the fluorescent X-ray analysis apparatus according to this invention, a change of the surface position of an irradiation object can be detected and the positions of the spectroscopic elements can be adjusted in accordance with the change surface position of the irradiation object. Therefore, even when the surface position of the irradiation object changes, the primary X-ray having necessary intensity for analysis can be accurately irradiated on the surface position of the irradiation object. This enables monitoring of components of various liquids having changing surface positions, the composition or thickness of a thin film and the like in an in-line process.

Embodiment 2

Figure 3:
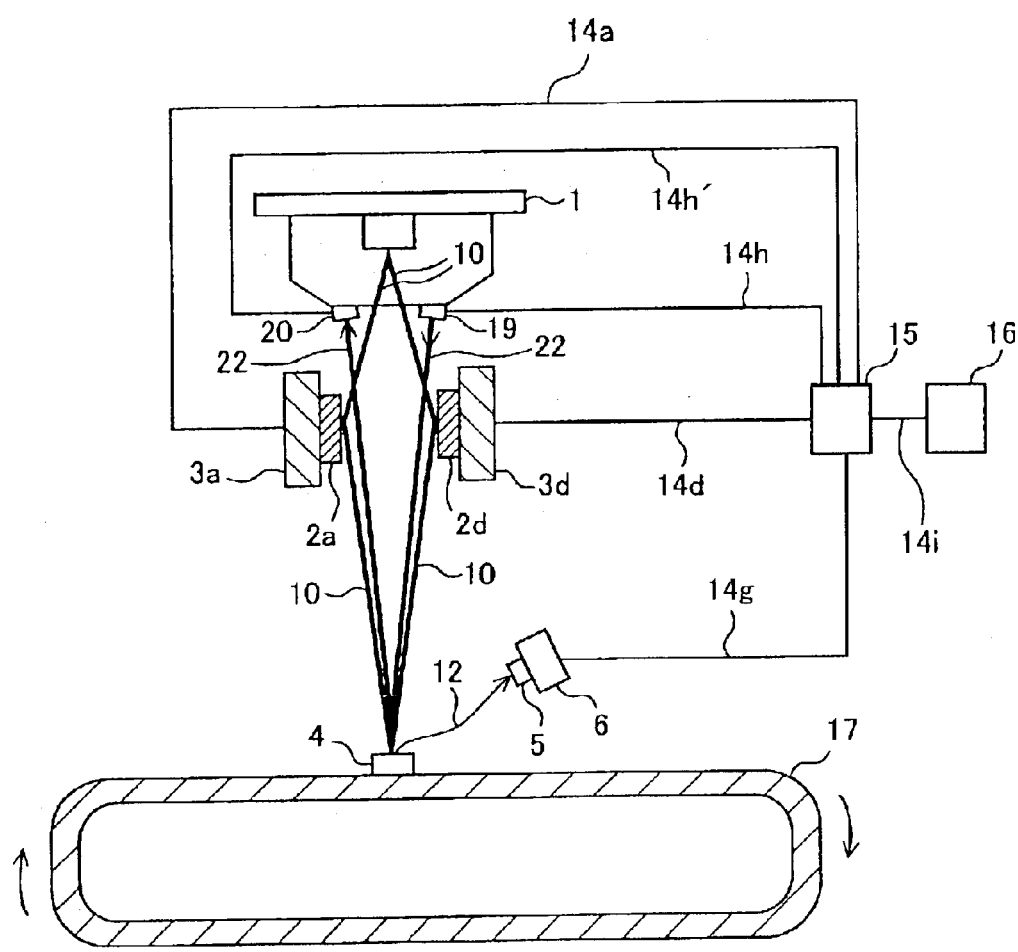
FIG. 3 is an explanatory view showing a cross-sectional structure of a fluorescent X-ray analysis apparatus according to this invention.

FIG. 3 is an explanatory view showing a cross-sectional structure of a fluorescent X-ray analysis apparatus according to this invention. In this embodiment, instead of the detection device for the surface position of a sample using the CCD camera in the apparatus described in Embodiment 1, a laser beam irradiating unit 19 and a laser beam detecting unit 20 are provided to measure the distance between an X-ray tube 1 and the surface of a sample 4 using a laser beam 22, thereby detecting the surface position of the sample and adjusting the positions of spectroscopic elements 2a to 2f. The laser beam irradiating unit 19, and the laser beam detecting unit 20 are connected with a control unit 15 by connection lines 14h and 14h' and the measured distance between the X-ray tube 1 and the surface of the sample 4 is communicated to the control unit 15. With this structure, though the sample surface cannot be visually monitored, a commercially available laser-based length measuring machine can be used. Particularly, it can be suitably used for a sample such as a semiconductor wafer having a flat sample surface and a constant angle in the horizontal direction.

While the laser beam irradiating unit 19 and the laser beam detecting unit 20 are provided to measure the distance between the X-ray tube 1 and the surface of the sample 4 in this embodiment, the measurement of the distance between the X-ray tube 1 and the surface of the sample 4 is not limited to this method. For example, the distance can also be measured by an acoustic wave-based length measuring machine having a combination of an ultrasonic irradiating unit and an ultrasonic detecting unit.

In the above-described Embodiments 1 and 2, the distance between the X-ray tube 1 and the surface of the sample 4 is measured by using one of the irradiation object surface position detecting unit using a so-called optical microscope structure including the camera unit 7a made up of the light source, the CCD camera and the detector and the monitor part 7b, the laser-based length measuring machine, and the acoustic wave-based length measuring machine. However, these irradiation object surface position detecting unit and the measuring machines can be used in combination, and in that case, the distance can be measured with higher accuracy.

As described above, with the fluorescent X-ray analysis apparatus according to this invention, the distance between the X-ray source and the sample surface is detected by the length measuring machine with respect to a sample with a changing surface position, and the positions of the spectroscopic elements are adjusted so that the primary X-ray is condensed on the changing surface position of the sample. Therefore, a fluorescent X-ray analysis apparatus capable of monitoring the concentration of a metal element in various liquids, the composition or thickness of a thin film and the like in an in-line process can be realized.

Embodiment 3

Figure 4A:
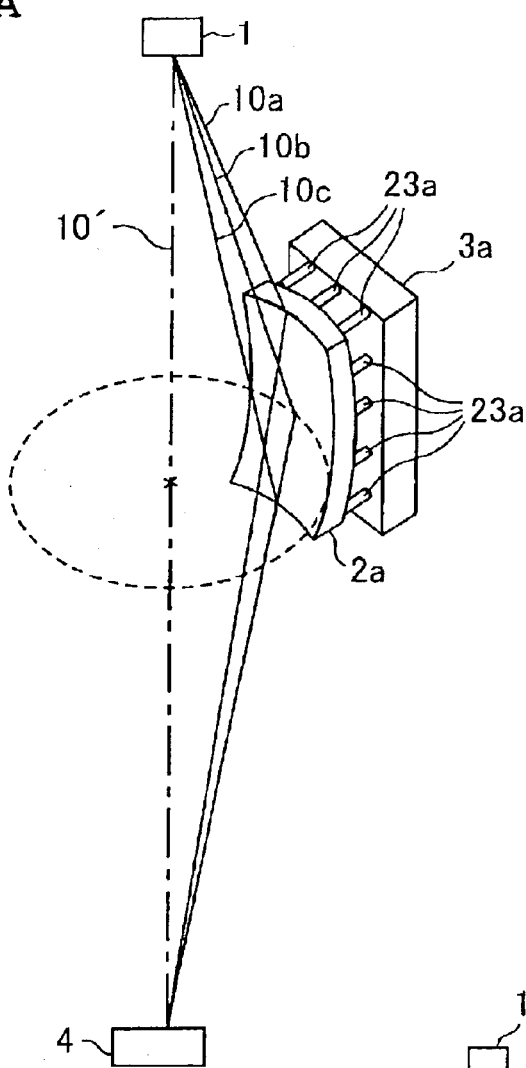
FIGS. 4A to 4C are explanatory views showing a structure of a fluorescent X-ray analysis apparatus according to this invention.
Figure 4B:
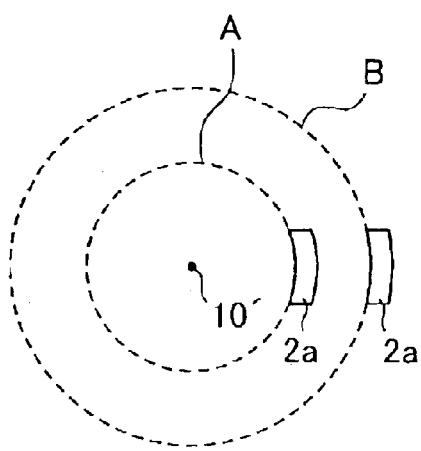
Figure 4C:
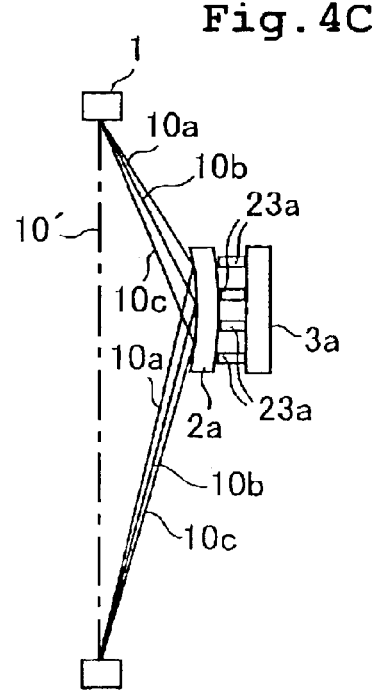

FIGS. 4A to 4C are explanatory views showing a structure of a fluorescent X-ray analysis apparatus according to this invention. In this embodiment, curved spectroscopic elements are used instead of the parallel plate-like spectroscopic elements of the apparatus described in Embodiment 1. Specifically, as shown in FIG. 4A, spectroscopic elements 2a to 2f are connected with spectroscopic element moving devices 3a to 3f via spectroscopic element curved shape adjusting means 23a to 23f including plural actuators and therefore can be adjusted to have a predetermined curved shape in accordance with a position change. FIG. 4A typically shows only the spectroscopic element 2a, the actuator 23a and the spectroscopic element moving device 3a. The actuators 23a to 23f are connected with a controller 5 by connection lines, not shown, and when the spectroscopic elements 2a to 2f move, the surfaces of the spectroscopic elements 2a to 2f are adjusted to have the following curved shape.

The spectroscopic elements 2a to 2f are caused to have a curved shape for the following reason. That is, if the spectroscopic elements are flat plate-like as in the above-described Embodiment 1, theoretically, only one point in each spectroscopic element satisfies the relation of equation (1). Therefore, normally, the irradiation intensity of the primary X-ray to the sample 4 is extremely lowered by monochromatizing the primary X-ray. However, as the flat plate-like spectroscopic elements are curved to form a circle about the optical axis of the primary X-ray, the position satisfying the above-described relation of equation (1) changes from a point to a line in the circumferential direction. That is, a portion satisfying equation (1) is generated on the entire circumference of the circle about the optical axis of the primary X-ray.

The significance of the curving of the spectroscopic elements is disclosed in detail in Japanese Laid-Open Patent Publication 2001-133421.

FIG. 4B shows the spectroscopic element 2a as viewed from a direction perpendicular to the optical axis of the primary X-ray, and shows a change of the curved state when the position of the spectroscopic element 2a is adjusted. When the spectroscopic element 2a is set at an inner position in FIG. 4B, the element is adjusted to a shape along a circle A. When the spectroscopic element 2B is set at an outer position in FIG. 4B, the element is adjusted to a shape along a circle B. As the spectroscopic element 2a is adjusted to such curved shapes, a portion satisfying the relation of equation (1) exists on the entire circumference.

Moreover, as the direction of irradiation with the primary X-ray (vertical direction in FIG. 4A) is adjusted to have an arc shape or a log-spiral curve shape as disclosed in Japanese Laid-Open Patent Publication 2001-133421, the above-described equation (1) can be satisfied in the entire direction of irradiation with the primary X-ray. FIG. 4C is a cross-sectional view of the spectroscopic element 2a as viewed from a direction parallel to the optical axis of the primary X-ray. In FIG. 4C, the spectroscopic element 2a has an arc or log-spiral curve-like cross-sectional shape. As the spectroscopic element 2a is curved into such a shape, all of primary X-rays 10a, 10b and 10c are condensed at one point on the surface of the sample 4, that is, at a center of optical axis 10' of the primary X-ray 10 on the surface of the sample 4. Therefore, by curving the flat plate-like spectroscopic elements to form a circle about the optical axis of the primary X-ray in the circumferential direction and curving the spectroscopic elements to have an arc shape or a log-spiral curve shape in the entire direction parallel to the optical axis of the primary X-ray, it is possible to monochromatize the primary X-ray while condensing the monochromatized primary X-ray at one point on the surface of the sample 4, that is, at the center of optical axis 10' of the primary X-ray on the surface of the sample 4, and to significantly improve the intensity per unit area of the primary X-ray.

As described above, with the fluorescent X-ray analysis apparatus according this invention, since the surface shape of the spectroscopic elements that are adjusted in position in accordance with a change of the surface position of the sample is caused to be a curved shape such that the relation of the Bragg's formula is satisfied between the X-ray tube and the surface of the sample, in addition to the effect obtained in Embodiment 1, the quantity of the monochromatized primary X-ray irradiated on the sample surface significantly increases and therefore the quantity of the secondary X-ray radiated from the sample surface significantly increases, thus further improving the detection accuracy.

What is claimed is:

1. A fluorescent X-ray analysis apparatus comprising:

an X-ray generation source for radiating a beam of primary X-rays;

plural spectroscopic elements having inner surfaces and circularly arranged so that their inner surfaces describe a circle centered on an optical axis of the beam of primary X-rays and for monochromatizing the beam of primary X-rays into a monochromatic beam of primary X-rays and condensing the beam of primary X-rays on a surface of an object irradiated by the beam;

spectroscopic element position adjusting means for adjusting positions of the plural spectroscopic elements;

a secondary X-ray detector for detecting secondary X-rays radiated from a surface of the irradiation object upon irradiation with the monochromatic beam of primary X-rays;

secondary X-ray detector position adjusting means for adjusting position of the secondary X-ray detector;

irradiation object surface position detecting means for detecting position of the surface of the irradiation object radiating the secondary X-rays; and control means for adjusting the positions of the plural spectroscopic elements by the spectroscopic element position adjusting means to condense the monochromatic beam of primary X-rays on the surface of the irradiation object, based on the position of the surface of the irradiation object detected by the irradiation object surface position detecting means.

2. The fluorescent X-ray analysis apparatus according to claim 1, wherein the control means adjusts the position of the secondary X-ray detector by using the secondary X-ray detector position adjusting means to increase the secondary X-rays detected, based on the position of the surface of the irradiation object.

3. The fluorescent X-ray analysis apparatus according to claim 2, wherein the secondary X-ray detector is one of a silicon drift semiconductor detector and plural PIN semiconductor detectors.

4. The fluorescent X-ray analysis apparatus according to claim 2, wherein the irradiation object surface position detecting means includes at least one of an optical microscope, a laser-based length measuring machine, and an acoustic wave-based length measuring machine.

5. The fluorescent X-ray analysis apparatus according to claim 4, wherein the secondary X-ray detector is one of a silicon drift semiconductor detector and plural PIN semiconductor detectors.

6. The fluorescent X-ray analysis apparatus according to claim 1, wherein the irradiation object surface position detecting means includes at least one of an optical microscope, a laser-based length measuring machine, and an acoustic wave-based length measuring machine.

7. The fluorescent X-ray analysis apparatus according to claim 6, wherein the secondary X-ray detector is one of a silicon drift semiconductor detector and plural PIN semiconductor detectors.

8. The fluorescent X-ray analysis apparatus according to claim 1, wherein the secondary X-ray detector is one of a silicon drift semiconductor detector and plural PIN semiconductor detectors.

* * * * *